US010228666B2

(12) United States Patent
Livingston et al.

(10) Patent No.: US 10,228,666 B2
(45) Date of Patent: Mar. 12, 2019

(54) MATERIAL MODIFICATION ASSEMBLY AND METHOD FOR USE IN THE MODIFICATION OF MATERIAL SUBSTRATES

(71) Applicants: The Aerospace Corporation, El Segundo, CA (US); Amendia Inc., Marietta, GA (US)

(72) Inventors: Frank Edward Livingston, Redondo Beach, CA (US); Timothy Ganey, Tampa, FL (US)

(73) Assignee: The Aerospace Corporation, El Segundo, CA (US)

( * ) Notice: Subject to any disclaimer, the term of this patent is extended or adjusted under 35 U.S.C. 154(b) by 730 days.

(21) Appl. No.: 14/163,712

(22) Filed: Jan. 24, 2014

(65) Prior Publication Data
US 2014/0228991 A1 Aug. 14, 2014

Related U.S. Application Data

(63) Continuation-in-part of application No. 13/767,055, filed on Feb. 14, 2013, now Pat. No. 8,679,189.
(Continued)

(51) Int. Cl.
G05B 19/37 (2006.01)
G05B 15/02 (2006.01)
A61F 2/30 (2006.01)

(52) U.S. Cl.
CPC .......... *G05B 15/02* (2013.01); *A61F 2/30771* (2013.01); *A61F 2002/3097* (2013.01)

(58) Field of Classification Search
USPC .......................................................... 700/97
See application file for complete search history.

(56) References Cited

U.S. PATENT DOCUMENTS

| 7,526,357 B2 * | 4/2009 | Livingston ......... | B23K 26/0626 438/689 |
| 2002/0072823 A1 * | 6/2002 | Belanger ............ | G05B 19/4142 700/159 |

(Continued)

OTHER PUBLICATIONS

Livingston, Frank E., et al, "Chapter 9: Laser Processing Architecture for Improved Material Processing"; *Laser Processing of Materials: Fundamentals, Applications, and Developments*, P. Schaaf Ed., Springer Series Materials Science, Springer-Verlag, Berlin; (2010), pp. 193-228.

*Primary Examiner* — Darrin D Dunn
(74) *Attorney, Agent, or Firm* — Manita Rawat; Duane Morris LLP

(57) ABSTRACT

A material modification assembly comprises an energy source for generating light beams to modify a substrate. A computing device generates pattern script(s) based on at least one parameter of the modification. The computing device also generates process script(s) including a type of pulse scripts to be used with the light beams and are based on at least one parameter of the interaction between the energy source and the substrate. The computing device combines the pattern script(s) with the process script(s) and generates command signals based on the combination. The computing device transmits the command signals to one or more additional devices of the material modification assembly to facilitate modifying the light beams for the modification to the substrate such that the modification includes a pattern on at least a surface of the substrate having dimensions and includes two or more discrete material alterations or changes spatially overlapped within the pattern.

22 Claims, 10 Drawing Sheets

Related U.S. Application Data

(60) Provisional application No. 61/763,223, filed on Feb. 11, 2013.

(56) References Cited

U.S. PATENT DOCUMENTS

| | | | |
|---|---|---|---|
| 2009/0188901 A1* | 7/2009 | Dantus | B23K 26/032 219/121.76 |
| 2011/0024400 A1* | 2/2011 | Rumsby | B23K 26/0732 219/121.61 |
| 2012/0328905 A1* | 12/2012 | Guo | B23K 26/0084 428/687 |

* cited by examiner

MATERIAL MODIFICATION ASSEMBLY AND METHOD FOR USE IN THE MODIFICATION OF MATERIAL SUBSTRATES

RELATED AND CO-PENDING APPLICATION

This application is a continuation-in-part of and claims priority to co-pending U.S. patent application Ser. No. 13/767,055 entitled BONE GROWTH ENHANCING IMPLANT filed Feb. 14, 2013, which claims the benefit of U.S. Provisional Application 61/763,223, filed Feb. 11, 2013, the disclosures of which are incorporated herein by reference in its entirety.

BACKGROUND

The embodiments described herein relate generally to a material modification assembly that includes a laser and can be used with systems, such as a bone growth enhancing implant system, to facilitate a modification to a material substrate using the laser such that the modification includes a pattern on at least a surface or in the interior or bulk of the material substrate having dimensions and the modification includes two or more discrete material alterations or changes spatially overlapped within the pattern. The modification can also include patterns that are discretely spaced or separated to create specific functionalities and have variable chemical and physical properties.

At least some known energy sources, such as lasers, can be used for modifying material properties, offering processing methods that are physically non-intrusive and capable of delivering spatially-focused and diffraction-limited action at a distance. As such, the lasers can be used in commercial manufacturing and industrial environments, with diverse applications, such as in the automotive, aeronautics, electronics, and medical industries. For example, the lasers can be used to modify various types of material substrates.

When modifying material substrates, the lasers provide a directed high-energy source to achieve a single process outcome. The single process outcome includes ablation, sintering, or texturing to create, for example, a design pattern on at least a surface of the material substrate. As such, the lasers can provide a single change or alternation to the material substrate. However, some industries want to perform multiple changes or modifications to the material substrate. When performing multiple changes or modifications, separate laser processes are required for each change. For example, a first process would be performed for ablation and, subsequently, a second process would be performed for sintering. As such, performing multiple changes or modifications to the material substrate with a laser can be expensive and time consuming

BRIEF DESCRIPTION

In one embodiment, a material modification assembly is provided and includes an energy source that is configured to generate a plurality of light beams for a modification to a material substrate. A computing device is coupled to the energy source. The computing device is configured to generate at least one pattern script for the modification to the material substrate, wherein the pattern script is based on at least one parameter of the modification. The computing device is also configured to generate at least one process script that includes a type of a plurality of pulse scripts to be used in conjunction with the light beams generated by the energy source for the modification to the material substrate, wherein the pulse scripts are based on at least one parameter of the interaction between the energy source and the material substrate. The computing device is configured to combine the pattern script with the process script and to generate a plurality of command signals that are based on the combination of the pattern script and the process script. The computing device is also configured to transmit the command signals to one or more additional component devices of the material modification assembly that are coupled to the computing device to enable the component device(s) to facilitate modifying the light beams being generated by the energy source for the modification to the material substrate such that the modification includes a pattern on at least a surface of the material substrate having dimensions and includes two or more discrete material alterations or changes spatially overlapped within the pattern. The modification can also include patterns that are discretely spaced or separated to create specific functionalities and have variable chemical and physical properties.

In another embodiment, a method for use in a modification of a material substrate is provided. The method includes coupling an energy source to a computing device. At least one pattern script for a modification to a material substrate is generated, via the computing device, wherein the pattern script is based on at least one parameter of the modification. At least one process script that includes a type of a plurality of pulse scripts to be used in conjunction with a plurality of light beams generated by the energy source for the modification to the material substrate is generated, via the computing device. The pulse scripts are based on at least one parameter of the interaction between the energy source and the material substrate. The pattern script is combined with the process script, via the computing device. A plurality of command signals that are based on the combination of the pattern script and the process script are generated, via the computing device. The command signals are transmitted to one or more additional component devices that are coupled to the computing device to enable the component device(s) to facilitate modifying the light beams being generated by the energy source for the modification to the material substrate such that the modification includes a pattern on at least a surface of the material substrate having dimensions and includes two or more discrete material alterations or changes spatially overlapped within the pattern. The modification can also include patterns that are discretely spaced or separated to create specific functionalities and have variable chemical and physical properties.

In yet another embodiment, a system is provided. The system includes a material substrate and a material modification assembly positioned proximate to the material substrate. The material modification assembly includes an energy source positioned proximate to the material substrate, wherein the energy source is configured to generate a plurality of light beams for a modification to the material substrate. A computing device is coupled to the energy source. The computing device is configured to generate at least one pattern script for the modification to the material substrate, wherein the pattern script is based on at least one parameter of the modification. The computing device is also configured to generate at least one process script that includes a type of a plurality of pulse scripts to be used in conjunction with the light beams generated by the energy source for the modification to the material substrate, wherein the pulse scripts are based on at least one parameter of the interaction between the energy source and the material substrate. The computing device is configured to combine the pattern script with the process script and to generate a plurality of command signals that are based on the combination of the pattern script and the process script. The computing device is also configured to transmit the command signals to one or more additional component devices of the material modification assembly that are coupled to the computing device to enable the component device(s) to facilitate modifying the light beams being generated by the energy source for the modification to the material substrate such that the modification includes a pattern on at least a surface of the material substrate having dimensions and includes two or more discrete material alterations or changes spatially overlapped within the pattern. The modification can also include patterns that are discretely spaced or separated to create specific functionalities and have variable chemical and physical properties.

DETAILED DESCRIPTION

The embodiments described herein include a material modification assembly that can be used with systems, such as a bone growth enhancing implant system, wherein the material modification assembly facilitates an efficient and cost-effective method for heterogeneous multi-material processing and for the expression of multiple functionalities on a single common base material substrate. The material modification assembly includes an energy source and a computing device that is used to modify the light beams being generated by the energy source for a modification to a material substrate. For example, in some embodiments, the computing device is configured to generate at least one pattern script for the modification to the material substrate and at least one process script that includes a type of a plurality of pulse scripts to be used in conjunction with the light beams generated by the energy source. The computing device is also configured to combine the pattern script with the process script and to generate a plurality of command signals that are based on the combination. The computing device is configured to transmit the command signals to one or more additional component devices of the material modification assembly that are coupled to the computing device to enable the component device(s) to facilitate modifying the light beams being generated by the energy source for the modification to the material substrate such that the modification includes a pattern on at least a surface of the material substrate having dimensions and includes two or more discrete material alterations or changes spatially overlapped within the pattern. The modification can also include patterns that are discretely spaced or separated to create specific functionalities and have variable chemical and physical properties. As such, multiple changes or modifications can be made to the material substrate without having to perform separate energy source processes for each change.

Figure 1A:
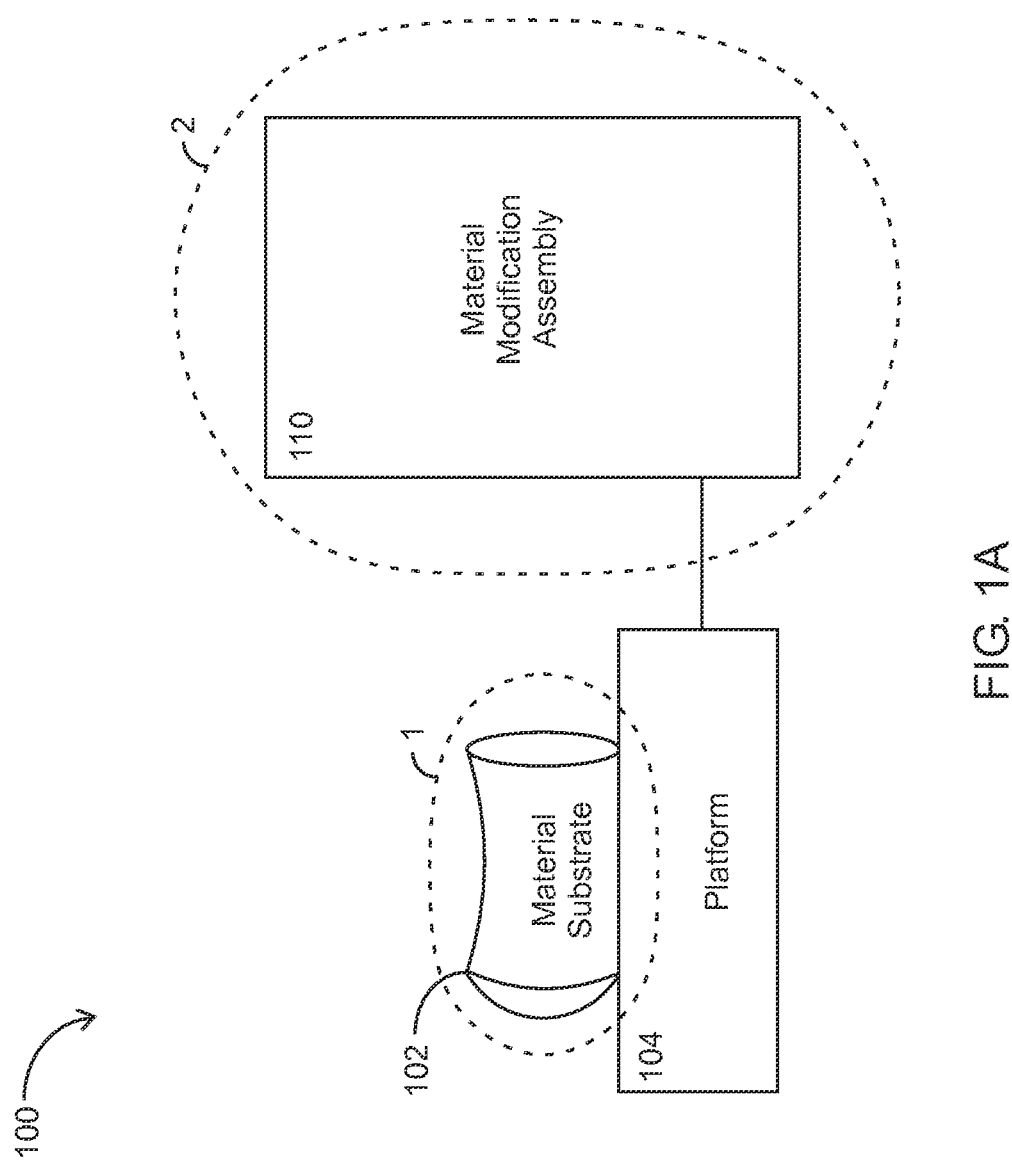
FIG. 1A is block diagram of an exemplary system that includes a material substrate.

FIG. 1A illustrates an exemplary system 100. In some embodiments, system 100 can be a bone growth enhancing system that is configured to design and create, for example, a bone implant device (not shown) that can be used on a mammal, such as a human. For example, in some embodiments, system 100 includes a material substrate 102 that is positioned on a platform 104, such as a surgical table, wherein material substrate 102 can be modified to form the bone implant device. In some embodiments, the bone implant device can be the bone implant device that is described in co-pending U.S. patent application Ser. No. 13/767,055 entitled BONE GROWTH ENHANCING IMPLANT filed Feb. 14, 2013, which is incorporated herein by reference in its entirety. It should be noted that the present disclosure is not limited to bone growth enhancing systems and one of ordinary skill in the art will appreciate that the current disclosure may be used in connection with other types of systems that are used to modify various types of material substrates. For example, in some embodiments, system 100 can be a power system that is used to modify, such as texturize, a metal component (not shown), such as a turbine.

Figure 1B:
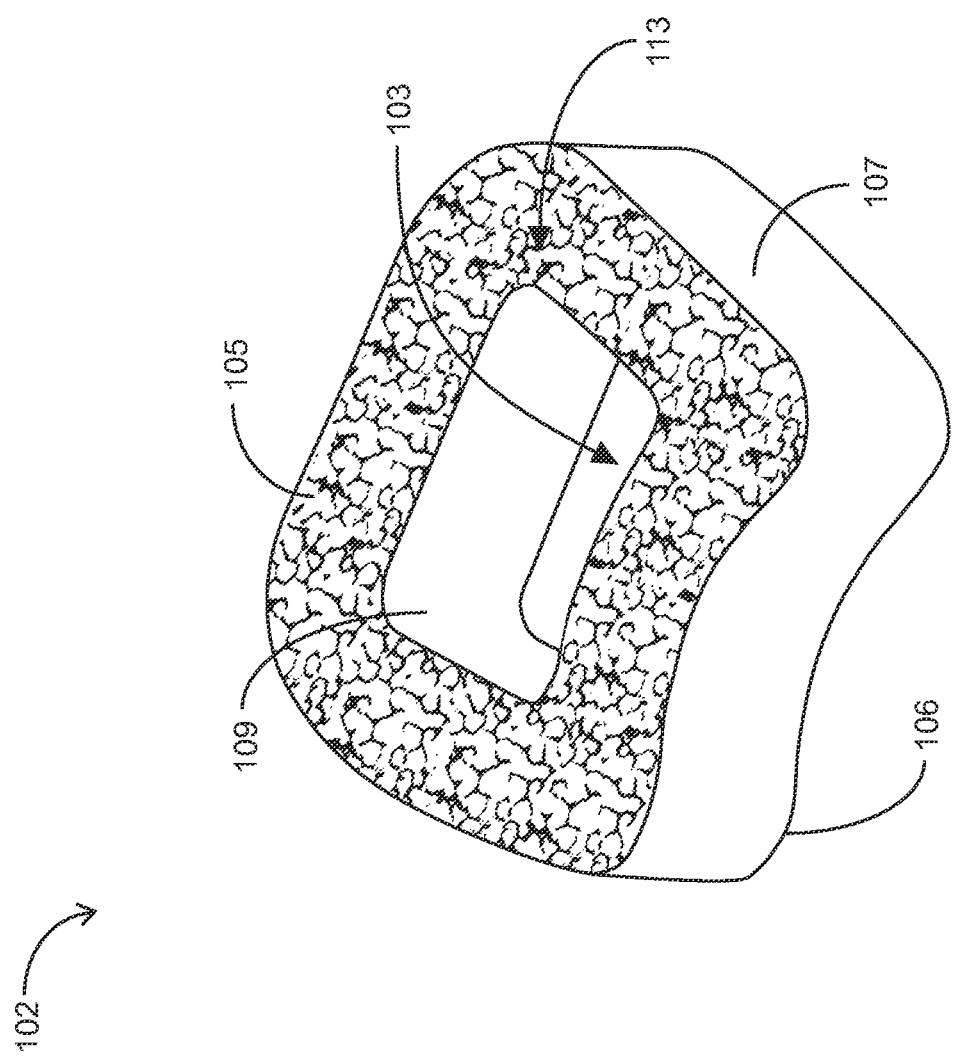
FIG. 1B is a perspective view of the material substrate shown in FIG. 1 and taken from area 1.

FIG. 1B illustrates material substrate 102 taken from area 1 (shown in FIG. 1A). Referring to FIG. 1B, material substrate 102 has a substantially cylindrical shape and a channel 103 is defined therein such that channel 103 extends through a top exterior surface 105 and a bottom exterior surface 106 of material substrate 102. A side exterior surface 107 substantially circumscribes at least a portion of material substrate 102 such that top exterior surface 105, bottom exterior surface 106, and channel 103 are not enclosed or covered by side exterior surface 107. In some embodiments, channel 103 is defined by an interior surface 109. In some embodiments, side exterior surface 107 and interior surface 109 can be made of an organic carbon or hydrocarbon base material that is synthetically produced, such as a polymer of a plastic material or a ceramic composition. In some embodiments, top exterior surface 105 and bottom exterior surface 106 can be composed of any implantable grade material, such as a polyether ether ketone (PEEK), polyether ketone ketone (PEKK), polyethylene, ultra high molecular weight polyethylene, polyphenylsulfone, polysulfone, polythermide, acetal copolymer, polyester woven or solid or implantable grade lennite UHME-PE or other suitable implant material. In other embodiments, top exterior surface 105 and bottom exterior surface 106 can be can be composed of naturally occurring materials, such as an allograft bone tissue used for implantation within a mammal Referring to FIG. 1A, system 100 also includes a material modification assembly 110 that is coupled to platform 104 such that material modification assembly 110 can be positioned proximate to material substrate 102. It should be noted that, as used herein, the term "couple" is not limited to a direct mechanical, thermal, communication, and/or an electrical connection between components, but may also include an indirect mechanical, thermal, communication and/or electrical connection between multiple components.

As described in more detail below with respect to the remaining figures, material modification assembly 110 is configured to modify material substrate 102 to create the bone implant device. For example, in some embodiments, material modification assembly 110 is configured to create a modification to at least a portion of top exterior surface 105 (shown in FIG. 1B) such that the modification includes a pattern having dimensions and includes two or more discrete material alterations or changes spatially overlapped within the pattern. The modification can also include patterns that are discretely spaced or separated to create specific functionalities and have variable chemical and physical properties. That is, material modification assembly 110 is configured for heterogeneous multi-material processing and for the expression of multiple functionalities on material substrate 102. Referring to FIG. 1B, the design patterns can be, for example, electrically conductive pathways or networks 113 on top exterior surface 105. In some embodiments, the modifications or design patterns can also be made on at least a portion of bottom exterior surface 106, side exterior surface 107, and/or interior surface 109. In some embodiments, the modifications or design patterns can be made in at least a portion of the material (not shown) between top exterior surface 105 and bottom exterior surface 106. In some embodiments, conductive pathways 113 can be the conductive pathways described in aforementioned U.S. patent application Ser. No. 13/767,055. In some embodiments, portions of material substrate 102 can be transformed or modified into electrically conductive pathways 113 and the remaining portions of material substrate 102 that are not in the pathways 102 can remain unaltered.

Figure 2:
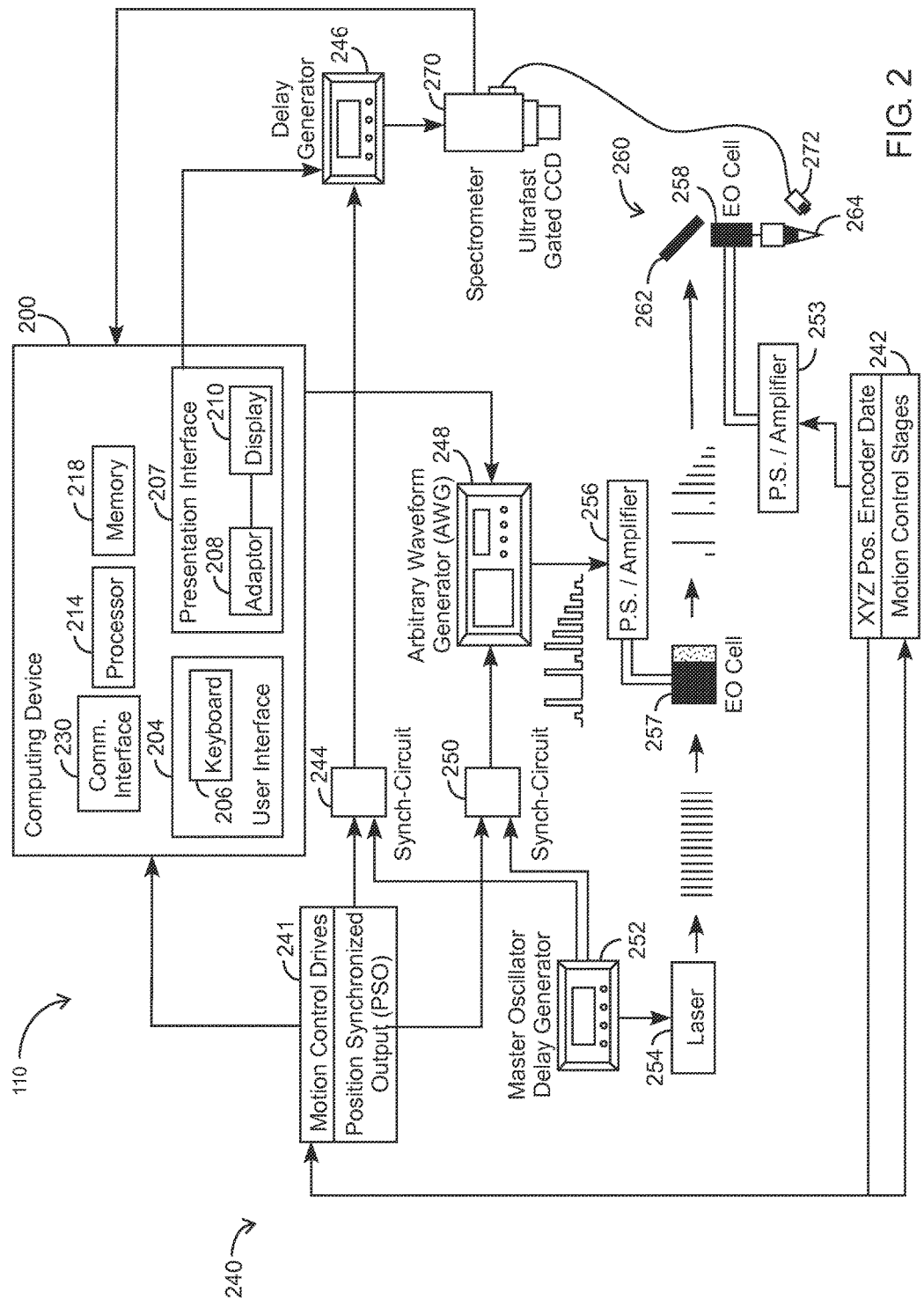
FIG. 2 is a block diagram of an exemplary material modification assembly that can be used with the exemplary system shown in FIG. 1 and taken from area 2.

FIG. 2 illustrates material modification assembly 110 taken from area 2 (shown in FIG. 1A). In some embodiments, material modification assembly 110 includes a computing device 200 that can be a physical desktop computer or host that includes a user interface 204 that receives at least one input from a user. In some embodiments, user interface 204 includes a keyboard 206 that enables the user to input pertinent information. In other embodiments, user interface 204 can include, for example, a pointing device, a mouse, a stylus, a touch sensitive panel (e.g., a touch pad or a touch screen), a gyroscope, an accelerometer, a position detector, and/or an audio input interface (e.g., including a microphone).

Moreover, in some embodiments, computing device 200 includes a presentation interface 207 that presents information, such as input events and/or validation results, to the user. In some embodiments, presentation interface 207 includes a display adapter 208 that is coupled to at least one display device 210. Display device 210 can be a visual display device, such as a cathode ray tube ("CRT"), a liquid crystal display ("LCD"), an organic LED ("OLED") display, and/or an "electronic ink" display. Alternatively, in other embodiments, presentation interface 207 can include an audio output device (e.g., an audio adapter and/or a speaker) and/or a printer.

Computing device 200 also includes a central processor 214 and at least one non-transitory, computer readable storage medium, such as a memory device 218. In some embodiments, processor 214 is coupled to user interface 204, presentation interface 207, and to memory device 218 via a system bus 220. In some embodiments, processor 220 communicates with the user, such as by prompting the user via presentation interface 207 and/or by receiving user inputs via user interface 204.

In the exemplary embodiment, processor 214 is programmed by encoding an operation using one or more executable instructions and providing the executable instructions in memory device 218. The term "processor" refers generally to any programmable system including systems and microcontrollers, reduced instruction set circuits ("RISC"), application specific integrated circuits ("ASIC"), programmable logic circuits ("PLC"), and any other circuit or processor capable of executing the functions described herein. The above examples are exemplary only, and thus are not intended to limit in any way the definition and/or meaning of the term "processor."

In the exemplary embodiment, memory device 218 includes one or more devices that enable information, such as executable instructions and/or other data, to be stored and retrieved. Moreover, in the exemplary embodiment, memory device 218 includes one or more computer readable media, such as, without limitation, dynamic random access memory ("DRAM"), static random access memory ("SRAM"), a solid state disk, and/or a hard disk. In the exemplary embodiment, memory device 218 stores, without limitation, application source code, application object code, configuration data, additional input events, application states, assertion statements, validation results, and/or any other type of data.

Computing device 200, in some embodiments, also includes a communication interface 230 that is coupled to processor 214 via system bus 220. Moreover, in the exemplary embodiment, communication interface 230 can be coupled to, for example, other components of material modification assembly 110 such that computing device 200 can communicate with the other components. Various connections are available between communication interface 230 of computing device 200 and other various components of material modification assembly 110. Such connections may include, without limitation, an electrical conductor, a low-level serial data connection, such as Recommended Standard (RS) 232 or RS-485, a high-level serial data connection, such as USB, a field bus, a PROFIBUS®, or Institute of Electrical and Electronics Engineers (IEEE) 1394 (a/k/a FIREWIRE), a parallel data connection, such as IEEE 1284 or IEEE 488, a short-range wireless communication channel such as BLUETOOTH, and/or a private (e.g., inaccessible outside system 100) network connection, whether wired or wireless. IEEE is a registered trademark of the Institute of Electrical and Electronics Engineers, Inc., of New York, N.Y. BLUETOOTH is a registered trademark of Bluetooth SIG, Inc. of Kirkland, Wash. PROFIBUS is a registered trademark of Profibus Trade Organization of Scottsdale, Ariz.

In some embodiments, computing device 200 is coupled to a motion control system 240 that includes motion control drives 241 and motion control stages 242. Motion control system 240 is coupled to a first synch circuit 244 that is coupled to a delay generator 246 and to a detection device, such as a spectrometer 270. In some embodiments, first synch circuit 244 can be any suitable commercially available circuit that is programmed to control the timing of signals being channeled through material modification assembly 110 based on information received from computing device 200. In some embodiments, spectrometer 270 can be any suitable commercially available spectrometer, detection device, sensing element or similar monitoring instrument.

In some embodiments, motion control system 240 is coupled to a second synch circuit 250 that is coupled to a waveform generator 248 and a master oscillator delay generator 252. In some embodiments, waveform generator 248 can be any suitable commercially available arbitrary waveform generator. Second synch circuit 250 can also be any suitable commercially available circuit that is programmed to control the timing of signals. In some embodiments, an energy source, such as a laser 254, is coupled to master oscillator delay generator 252. In some embodiments, laser 254 can be any suitable laser that is configured to generate a plurality of pulsed light beams. In some embodiments, other types of energy sources can be used instead of lasers, such as electron beams, x-rays, proton beams, and lamp and arc sources.

In some embodiments, waveform generator 248 is also coupled to an amplifier 256 and motion control system 240 is coupled to an amplifier 253. In some embodiments, amplifiers 253 and 256 are each configured to alter any signals received therein. The signals can be altered according to a transfer function, such as to apply a gain factor to multiply the voltage or current or numerically digitized amplitude of the signals received therein to generate modified output signals, such as an amplified signals.

In some embodiments, material modification assembly 110 also includes one or more modulating devices, such as a first electro-optic (EO) modulator cell 257 and a second EO modulator cell 258. First EO modulator cell 257 is coupled to amplifier 256 in some embodiments. Second EO modulator cell 258 is coupled to a an optical assembly 260 that includes an optical device, such as a lens or mirror 262, and a focusing conduit 264 to focus the light beams that go through lens 262 onto material substrate 102 (shown in FIGS. 1A and 1B). For example, in some embodiments, the light beams are focused onto at least a portion of top exterior surface 105 (shown in FIG. 1B), bottom exterior surface 106 (shown in FIG. 1B), and/or side exterior surface 107 (shown in FIG. 1B). In some embodiments, when other types of energy sources are used instead of laser 254, they can be modulated by devices other than EO cell modulators 257 and 258 to generate scripts of the other energy types, such as electron scripts, proton scripts, x-ray scripts etc.

Spectrometer 270 is positioned proximate to material substrate 102 such that a sensing element or a transducer 272 of spectrometer 270 is coupled to at least a portion of material substrate 102. Spectrometer 270 is also coupled to computing device 200. In some embodiments, spectrometer 270 is configured to detect various aspects of the modification being performed on material substrate 102.

During operation, material modification assembly 110 facilitates an efficient and cost-effective method for heterogeneous multi-material processing and for the expression of multiple functionalities on material substrate 102. As explained in more detail below with respect to the remaining figures, computing device 200 is used to modify the light beams being generated by laser 254 for the modification to material substrate 102. For example, in some embodiments, computing device 200 transmits command signals to one or more additional component devices of material modification assembly, such as motion control system 240, to facilitate modifying the light beams being generated by laser 254 for the modification to material substrate 102 such that the modification includes a pattern on at least a surface of the material substrate having dimensions and includes two or more discrete material alterations or changes spatially overlapped within the pattern. The modification can also include patterns that are discretely spaced or separated to create specific functionalities and have variable chemical and physical properties. As such, multiple changes or modifications can be made to material substrate 102 without having to perform separate laser processes for each change.

Figure 3:
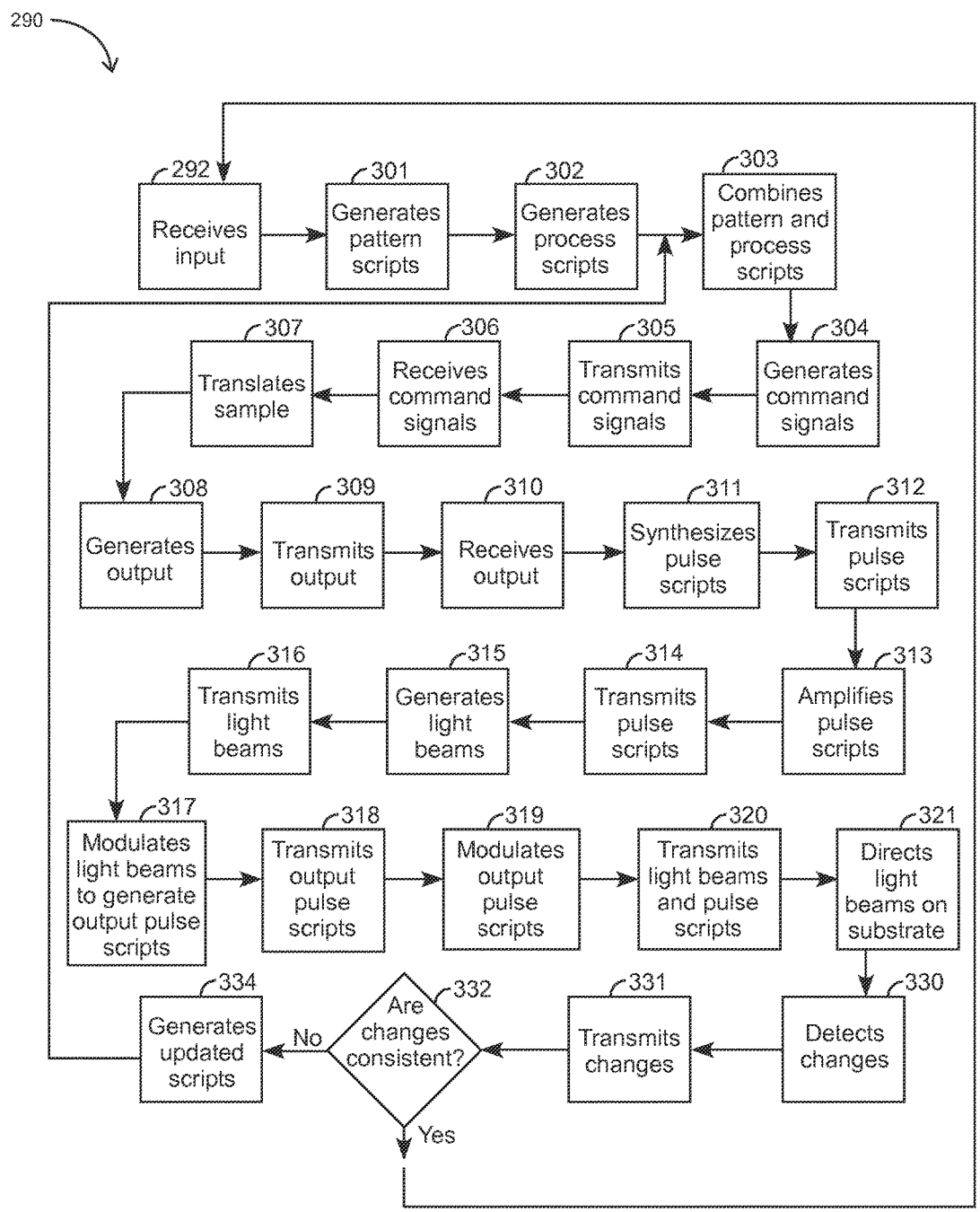
FIG. 3 is a flow diagram of an exemplary method that can be used for a modification of the material substrate using the material modification assembly shown in FIG. 2.

FIG. 3 is a flow diagram 290 of an exemplary method for use in the modification of a material substrate, such as material substrate 102 (shown in FIGS. 1A and 1B), using material modification assembly 110 (shown in FIGS. 1A and 2). In step 292, computing device 200 (shown in FIG. 2) receives an input from a user to modify material substrate 102. In some embodiments, the desired modification can be creating design patterns, such as conductive pathways 113 (shown in FIG. 1B), on at least a portion of top exterior surface 105 (shown in FIG. 1B) pursuant to various different desired parameters for pathways 113, such as desired dimensions and/or desired chemical and/or physical properties. In some embodiments, the desired modifications or design patterns can also be for the bottom exterior surface 106 (shown in FIG. 1B), side exterior surface 107 (shown in FIG. 1B), and/or interior surface 109 (shown in FIG. 1B) of material surface 102.

Based on the input, computing device 200 generates one or more pattern scripts in step 301. In some embodiments, each pattern script includes at least one parameter of the desired modification that is intended to be made on material substrate 102. For example, in some embodiments, each pattern script includes three-dimensional (3D) x-y-z- Cartesian coordinates and tool path segments that correspond to the overall geometry of the pattern.

In step 302, computing device 200 generates one or more process scripts. In some embodiments, each process script includes all relevant laser material processing parameters that will be applied for the modification. For example, the process scripts include laser pulse sequencing or genotype pulse scripts for the modification to material substrate 102. The process scripts also include the types of processing being used for the modification (e.g., ablation, annealing, texturing), material properties of material substrate 102 and/or modification (e.g., chemical, physical), pre-and post-laser treatment history (e.g., sintering, annealing, chemical passivation), and interactions between material substrate and laser 254 (shown in FIG. 2) (e.g., physical, chemical). The pulse scripts are based on the underlying chemical physics, solid-state dynamics and photochemistry associated with the interactions between laser 254 and material substrate 102.

As will be described in more detail below, the pulse scripts can be tailored and designed to elicit a diverse array of material modifications and inductions from the macroscale to the nanoscale. Such material modification and inductions include, but are not limited to, physical effects, such as patterning, structuring, texturing, morphology and topography, compaction and densification, mechanical strength and compliance. Chemical effects are also included, such as phase, composition and stoichiometry, ferroelectric, pyroelectric and piezoelectric behavior, magnetic induction and electrical conductivity.

Computing device 200, in step 303, combines or links the pattern script(s) with the process script(s). In order to combine the pattern scripts with the process scripts, in some embodiments, processor 214 (shown in FIG. 2) of computing device 200 is programed via, for example, software modules (not shown) that facilitate such processing. For example, in some embodiments, computer-assisted design (CAD) and manufacturing (CAM) software that define the 3D pattern geometry and tool path motion can be used and processor 214 can be programmed such that the end user is enabled to select the type and spatial location of the modification.

Moreover, processor 214 can be programmed to facilitate the interleaving of the pattern script(s) and the process script(s) to create the master control code, wherein the process script(s) (and all laser processing parameters and individual pulse scripts) have been linked in a line-by-line arrangement to the tool path geometry. The process script and pattern script linking or merging ensures that each delineated element (generally equivalent to the laser spot size) in the 3D specimen (i.e., material substrate 102) receives the correct and predefined laser pulse scripts that are required for the intended set of outcomes. The linking also facilitates the spatial and temporal overlap of the laser pulse scripts and material modifications. The modification can also include patterns that are discretely spaced or separated to create specific functionalities and have variable chemical and physical properties. The chemical and physical modifications can be created, for example, on at least a portion of top exterior surface 105, bottom exterior surface 106, side exterior surface 107, and/or interior surface 109 of material substrate 102.

In step 304, computing device 200 generates a plurality of command signals that are based on the combination of the pattern script(s) and the process script(s) and, in step 305, computing device 200 transmits the command signals to the other components of material modification assembly 110. In some embodiments, the command signals can be transmitted simultaneously to each of the other components. Alternatively, in other embodiments, the command signals can be transmitted in a sequential order, such as numerical order, to the other components.

In some embodiments, the command signals are representative of the various functions that each of the other components are to perform to ensure the desired modification is performed onto material substrate 102 based on the combined pattern script(s) and the process script(s). For example, the command signals can be representative of various functions that each of the other components are to perform to facilitate a modification that includes a pattern on at least a portion of a surface, such as top exterior surface 105 of material substrate 102, having dimensions and includes two or more discrete material alterations or changes spatially overlapped within the pattern. The modification can also include patterns that are discretely spaced or separated to create specific functionalities and have variable chemical and physical properties.

For example, in step 306, motion control system 240 (shown in FIG. 2) receives at least one of the command signals. In some embodiments, motion control drive 241 (shown in FIG. 2) receives the signal and, in step 307, motion control drive 241 translates at least a portion of a sample of material substrate 102 into a 3D coordinate system, such as a 3D x-y-z Cartesian coordinate system. In some embodiments, the sample of material substrate 102 is positioned within a holder (not shown) of motion control drive 241.

After the translation, in step 308, motion control drive 241 generates at least one output that provides instructions for the type of the plurality of pulse scripts to use for the modification to material substrate 102, wherein the instructions are based on the command signal that is received. For example, in some embodiments, the instructions can be instructions on how to modulate the pulse scripts for the intended modification. In step 309, motion control drive 241 transmits a signal representative of the output to waveform generator 248 (shown in FIG. 2) via second synch circuit 250 (shown in FIG. 2). In some embodiments, second synch circuit 250 facilitates transmitting the signals based on the command signals that it receives from computing device 200.

Figure 4:
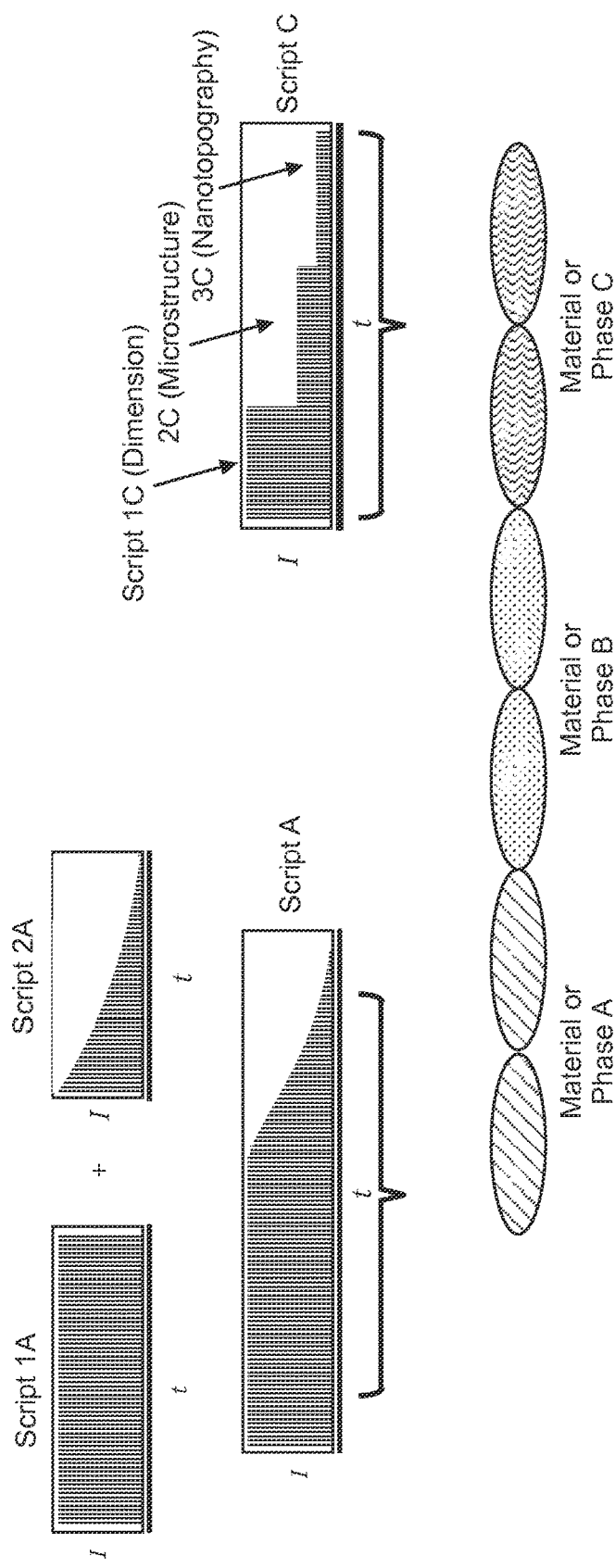
FIG. 4 is a diagram of exemplary events that can be performed by the material modification assembly shown in FIG. 2.

In step 310, waveform generator 248 receives the signal representative of the output. In step 311, waveform generator 248 synthesizes the pulse scripts based on the output. For example, FIG. 4 illustrates a diagram of an exemplary synthesis of pulse scripts by waveform generator 248, wherein each pulse script is shown as intensity (I) versus time (t). Referring to FIG. 4, in some embodiments, a first pulse script, such as Script 1A, is combined with a second pulse script, such as Script 2A, by waveform generator 248, to form a final pulse script that is used, such as Script A. Similarly, another group of pulse scripts, such as Scripts 1C, 2C, and 3C can be combined to form another final pulse script, such as Script C. In some embodiments, each of the individual scripts corresponds to a different parameter of the intended modification. For example, Script 1C corresponds to the dimension of the pattern or modification, Script 2C corresponds to the microstructure of the pattern or modification, and Script 3C corresponds to the nanotopography of the pattern or modification. In some embodiments, each final script, such as Script A and Script C, are used for each different material or phase of modification for material substrate 102. For example, Script A can be used for Material or Phase A and Script C can be used for Material or Phase C.

Referring to FIG. 3, in some embodiments, such as in step 312, the newly synthesized pulse scripts are transmitted to amplifier 256 (shown in FIG. 2). In step 313, the transmitted pulse scripts are then amplified via amplifier 256. The newly synthesized and amplified pulse scripts are then transmitted to first EO modulator cell 257 (shown in FIG. 2) in step 314.

In step 315, laser 254 generates a plurality of light beams based on signals received from master oscillator delay generator 252 (shown in FIG. 2). In some embodiments, master oscillator delay generator 252 facilitates the generation of the light beams based on command signals received from computing device 200. In step 316, laser 254 transmits the light beams to first EO modulator cell 257. In step 317, first EO modulator cell 257 modulates the light beams from laser 254 to create the output pulse scripts pursuant to the desired modification (i.e., based on the command signals received from computing device 200). In some embodiments, synch circuit 250 facilitates the timing of the transmission of the amplified pulse scripts (step 314) and light beams (step 316) to first EO modulator cell 257 to ensure synchronization of the modulated pulse script delivery to the desired location on the material substrate 102.

After receiving the pulse scripts and the light beams, first EO modulator cell 257 transmits the output pulse scripts to second EO modulator cell 258 in step 318. After receiving the output pulse scripts from first EO modulator cell 257, second EO modulator cell 258 further modulates the output pulse scripts pursuant to the desired modification in step 319 (i.e., based on the command signals received from computing device 200 and motion control system 240). In some embodiments, this further modulation changes the polarization of the light beams. Accordingly, in steps 313 to 319, the pulse scripts can be modulated, for example, in amplitude (intensity), pulse duration (pulse width), frequency (repetition rate), and/or polarization (electric-field orientation), or any combination thereof to facilitate the changes of the light beams, which may be needed to achieve the desired modification.

In step 320, second EO modulator cell 258 transmits the light beams combined with the further modulated output pulse scripts to optical assembly 260 (shown in FIG. 2). In step 321, optical assembly 260 directs the light beams onto material substrate 102, such as, for example, at least a portion of top exterior surface 105 of material substrate 102 to create the modification onto at least the portion of surface 105 such that the modification includes a pattern on at least a surface of material substrate 102 having dimensions and includes two or more discrete material alterations or changes spatially overlapped within the pattern. The modification can also include patterns that are discretely spaced or separated to create specific functionalities and have variable chemical and physical properties. In another embodiment, optical assembly 260 can direct the light beams onto other portions of material substrate 102, such as bottom exterior surface 106, side exterior surface 107, and/or interior surface 109 to facilitate the same modification.

Figure 5:
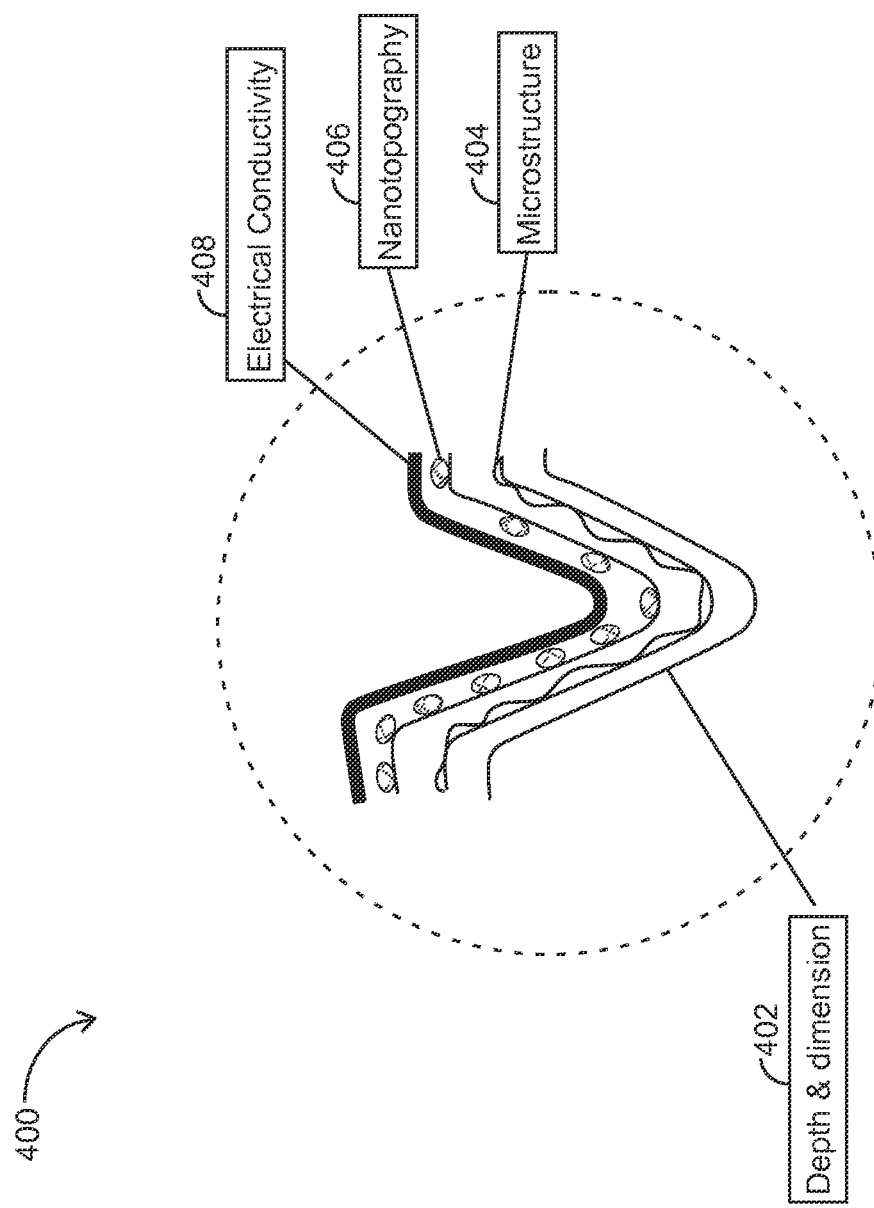
FIG. 5 is a diagram of a portion of an exemplary modification to the material substrate that can be performed by the material modification assembly shown in FIG. 2.

FIG. 5 illustrates an exemplary portion of a 3D design pattern 400 that can be created when optical assembly 260 directs the light beams onto, for example, top exterior surface 105 of material substrate 102. For example, referring to FIG. 5, there are two or more discrete material alterations or changes spatially overlapped within pattern 400. For example, there is a first material change 402 that pertains to the depth and dimension that is added and/or changed to modify material substrate 102. There is a second material change 404 that includes the microstructure that is added and/or changed to modify material substrate 102. There is a third material 406 change that is the nanotopography that is added and/or changed to modify material substrate 102. The fourth material change 408 is the electrical conductivity added and/or changed to modify material substrate 102.

As such, this method can impart various different material processes, such as imparting a 3D pattern to material substrate 102, a dimension to the 3D pattern, a microstructure to the dimension, a nanotopography to the microstructure, chemical and physical changes aligned with the 3D pattern, chemical and physical changes via both thermal and non-thermal pathways, and electrical activity to material substrate 102, which is in spatial and temporal resonance with the pattern, dimension, microstructure, and nanotopography.

Referring to FIG. 3, the modification being done to material substrate 102 can be monitored in real-time. For example, in step 330, spectrometer 270 (shown in FIG. 2) can detect the changes being made to material substrate 102, such as detecting the various chemical and physical property changes to material substrate 102. In step 331, spectrometer 270 transmits a signal representative of the detected changes to computing device 200. After receiving the detected changes, computing device 200 determines whether the detected changes are consistent with the desired modification that was requested by the user in step 332. If the detected changes are deemed consistent, then computing device 200 lets the method continue. If, however, the detected changes are not deemed consistent, then computing device 200 generates one or more updated pattern scripts and one or more updated process scripts in step 334, and these updated pattern scripts and process scripts are used for the process as steps 303 to 332 are repeated until the desired modification is created on material substrate 102.

Accordingly, as compared to known systems that are used to modify material substrates, the embodiments described herein facilitate an efficient and cost-effective method for heterogeneous multi-material processing and for the expression of multiple functionalities on a single common base material substrate. The embodiments described herein include a material modification assembly that can be used with systems, such as a bone growth enhancing implant system. The material modification assembly includes an energy source and a computing device that is used to modify light beams being generated by the energy source for a modification to a material substrate. For example, in some embodiments, the computing device is configured to generate at least one pattern script for the modification to the material substrate and at least one process script that includes a type of a plurality of pulse scripts to be used in conjunction with the light beams generated by the energy source. The computing device is also configured to combine the pattern script(s) with the process script(s) and to generate a plurality of command signals that are based on the combination. The computing device is configured to transmit the command signals to one or more additional component devices of the material modification assembly that are coupled to the computing device to enable the component device(s) to facilitate modifying the light beams being generated by the energy source for the modification to the material substrate such that the modification includes a pattern on at least a surface of the material substrate having dimensions and includes two or more discrete material alterations or changes spatially overlapped within the pattern. The modification can also include patterns that are discretely spaced or separated to create specific functionalities and have variable chemical and physical properties. As such, multiple changes or modifications can be made to the material substrate without having to perform separate energy source processes for each change.

Figure 6A:
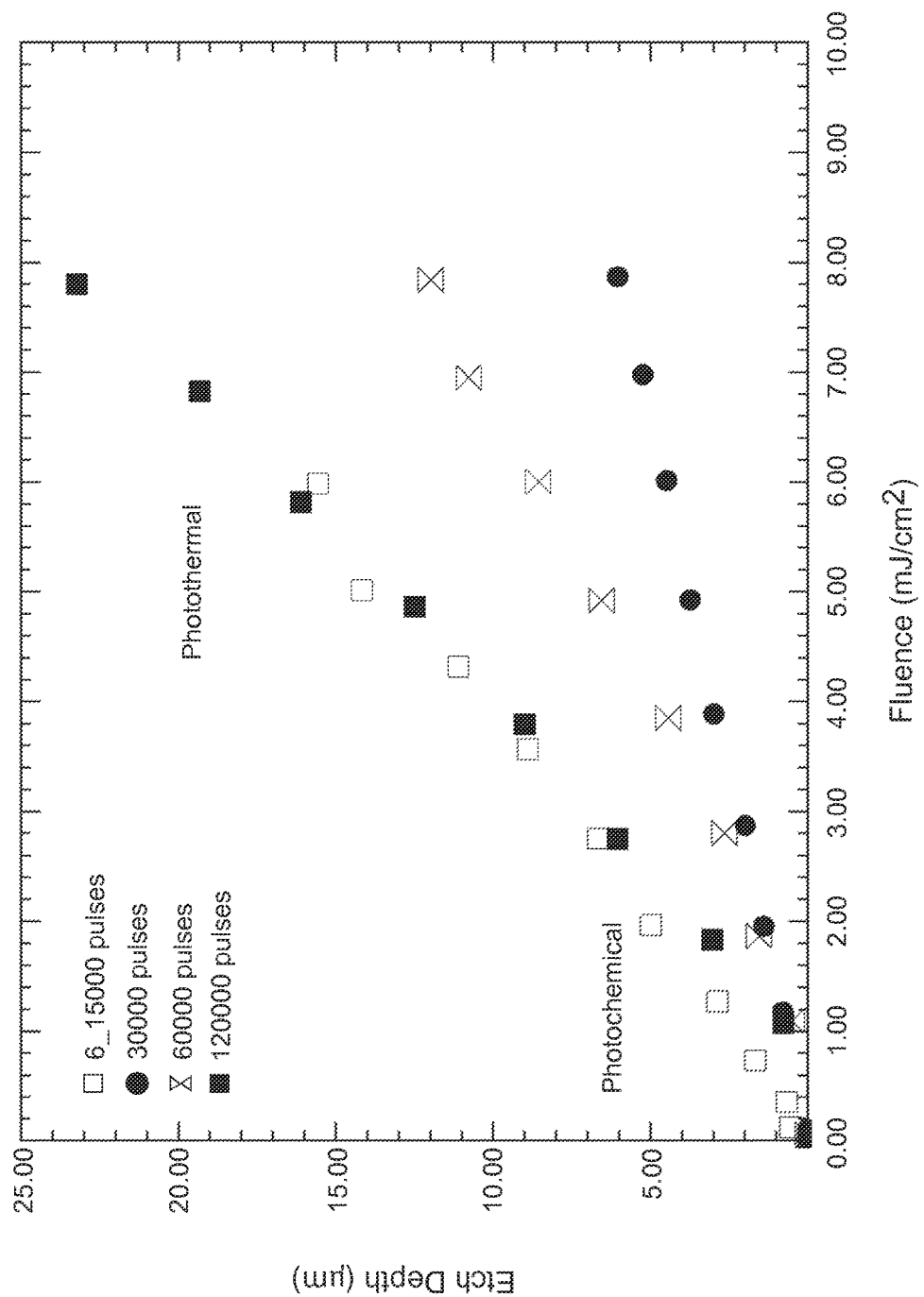
FIGS. 6A-6D are graphical representations of exemplary events that can be performed by the material modification assembly shown in FIG. 2.

In some embodiments, the laser patterned biogeometries described herein can be created using concatenated pulse sequences that can be based on the laser-PEEK interactions physics and can be specially designed for overlapping multiple discrete material alterations. For example, FIG. 6A is an exemplary graphical representation that describes the measured PEEK etch depths (micrometers($\mu$m)) vs. the laser fluence (milliJoules(mJ)/centimeter(cm)$^2$) using laser pulse script sequences ranging from 30000 pulses to 120000 pulses. As illustrated in FIG. 6A, the initial sets of pulses sequences (subset of the composite pulse script) can be used to variably control the depth and dimension of the pattern over several hundred micrometers with sub-micrometer-scale resolution and reproducibility. The pulse scripting approach enables control of energy flow into the PEEK polymer, and enables selection and regulation of the competing ablation mechanisms. Etch depths and dimensions could be defined through non-thermal (photochemical) and thermal (photothermal) pathways, and exclusively achieved through a single reaction channel or a combination of non-thermal and thermal pathways.

Figure 6B:
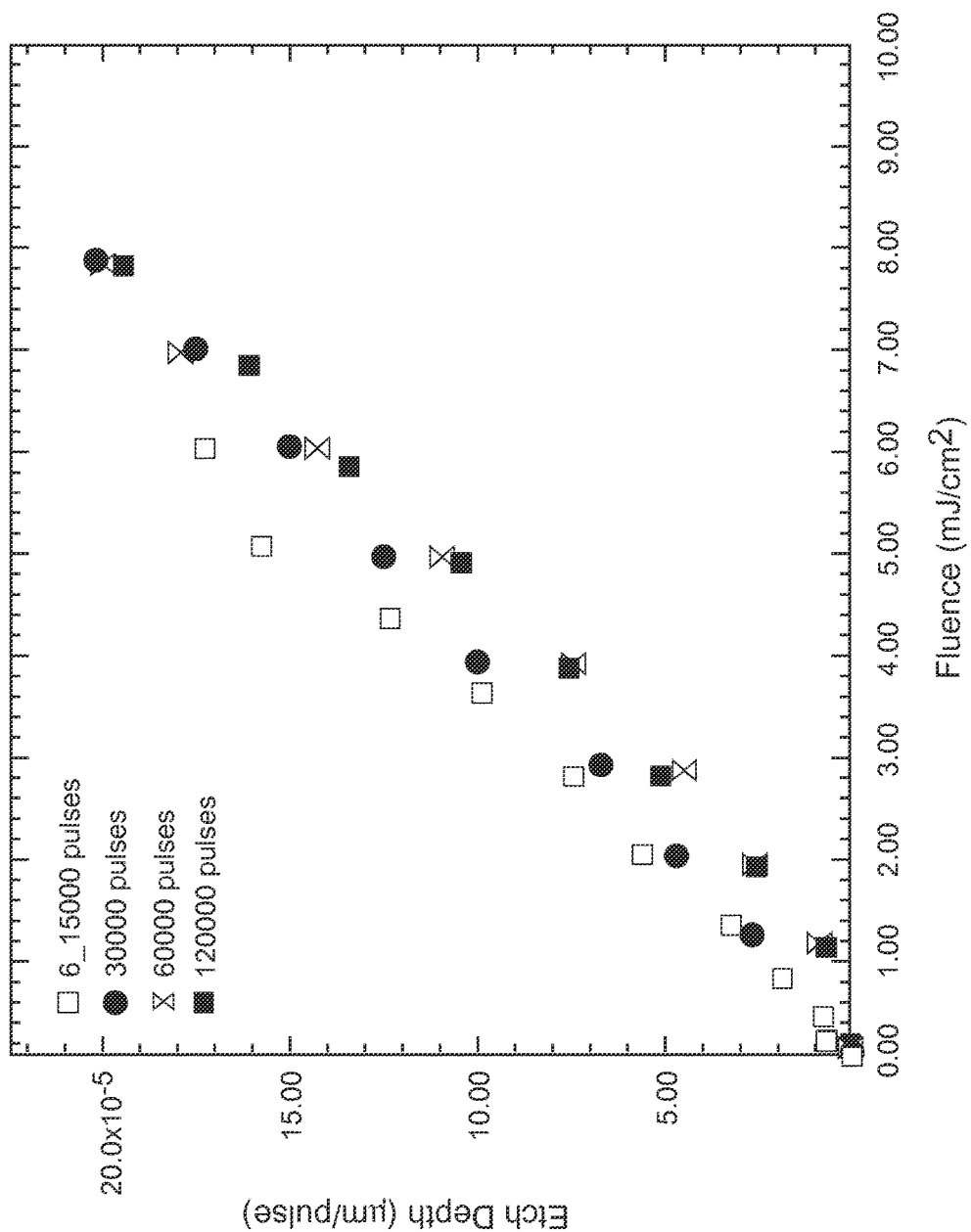

In some embodiments, the pulse scripting approach permits exquisite control of energy flow into for example, a polymer system, and enables selection and regulation of the competing ablation mechanisms. For PEEK, for example, pulse scripting can enable material removal and etch depths to be defined through non-thermal (photochemical) and thermal (photothermal) pathways. In some embodiments, the depths and dimensions could he achieved exclusively through a single reaction channel or a combination of non-thermal and thermal pathways. For example, FIG. 6B is another exemplary graphical representation that describes calculated etch rates vs. laser fluence (mJ)/(cm)$^2$ using laser pulse script sequences ranging from 30000 pulses to 120000 pulses. The etch rates can be derived from corresponding etch depths shown in FIG. 6A. As illustrated in FIG. 6B, high fidelity inter- and intra--pulse modulation within the pulse scripts enables the precise removal of material during patterning. Laser scripted processing can facilitate ultrafast transient heating of the material via time-dependent relaxation processes for efficient energy coupling and high spatial selectivity. PEEK etch rates can be effectively controlled with a per-pulse resolution below 1-nanometer.

Figure 6C:
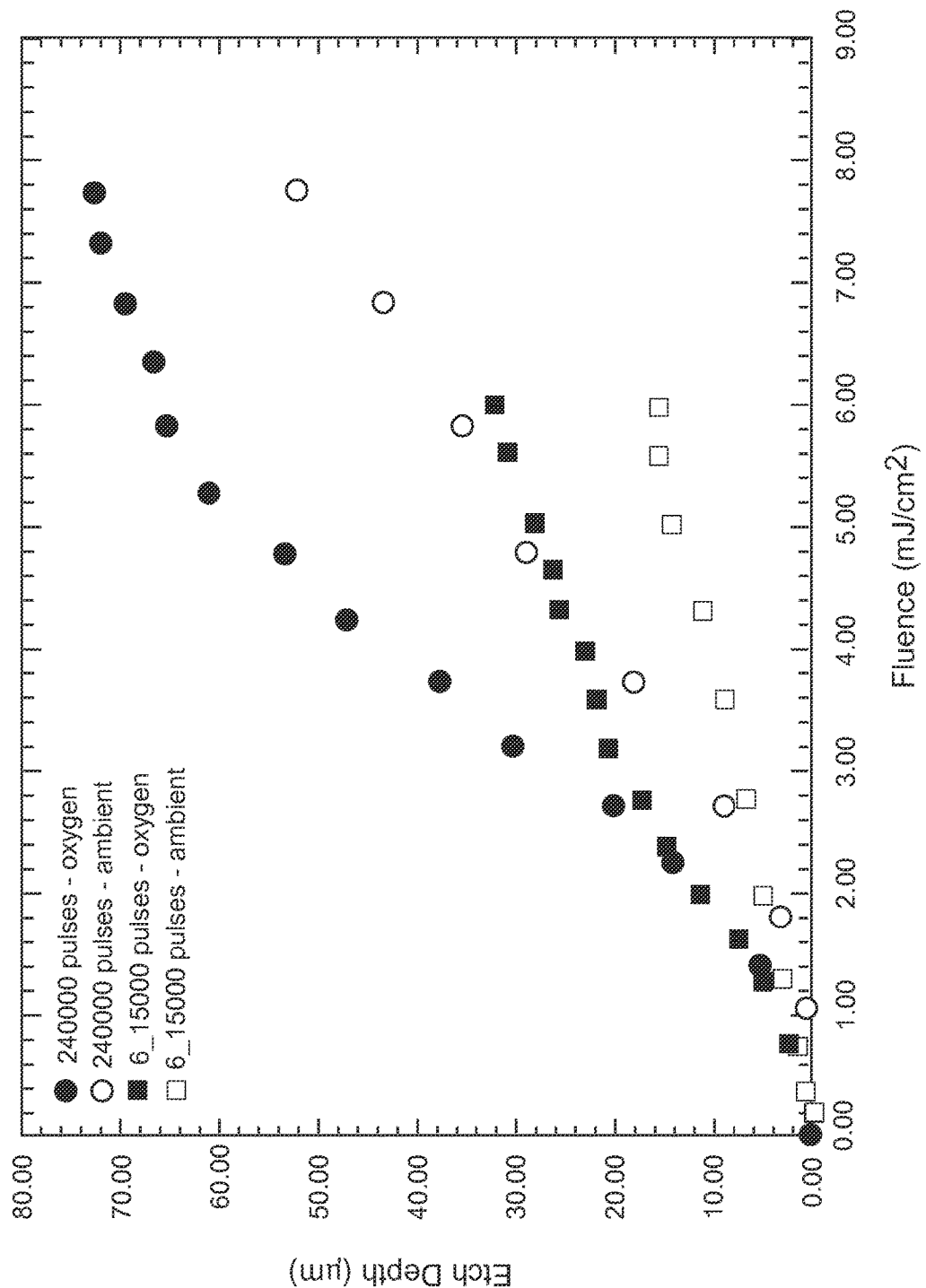

In sonic embodiments, the laser-scripted etching rates could be enhanced or altered through the use of purge gases during photon exposure and pulse-modulated patterning. The pulse scripts and environmental processing conditions can be used in combination to effectively guide the laser-PEEK reaction pathways, enabling selective control of the etch kinetics, surface chemistry, structure and composition. For example, FIG. 6C is another exemplary graphical representation that describes measured PEEK etch depths (µm) vs. the laser fluence (mJ)/(cm)² using laser pulse script sequences under various gas purging conditions. As illustrated in FIG. 6C, the pulse scripts and environmental processing conditions can be used in combination to effectively guide the laser-PEEK reaction pathways, enabling selective control of the etch kinetics, surface chemistry, structure and position. As shown in FIG. 6C, laser-scripted processing in an oxygen-rich environment can increase the etching rates by approximately a factor of three compared to processing under ambient conditions.

Figure 6D:
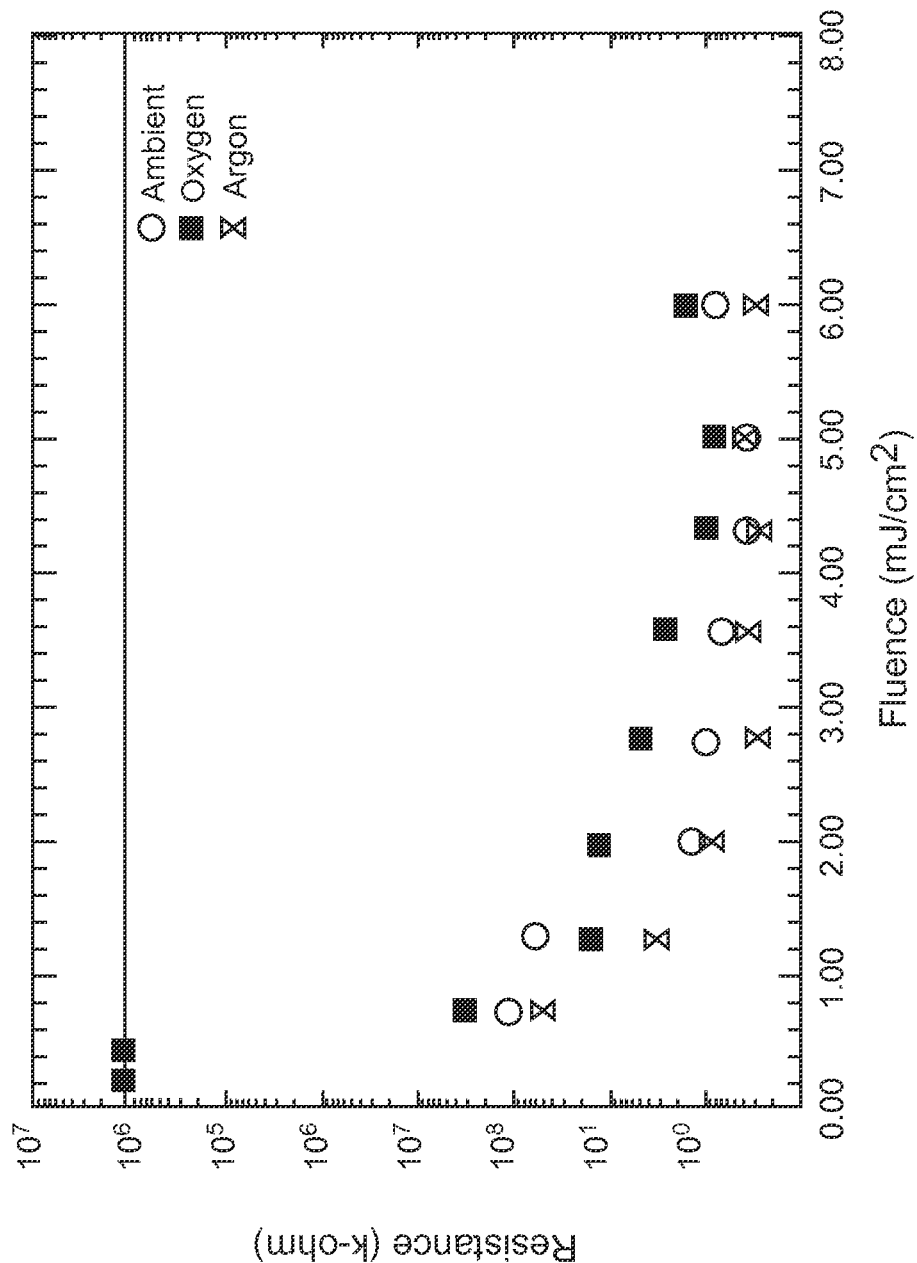

In some embodiments, prescribed pulse sequences can enable the control of the surface chemistry, oxygen/carbon ratios, carbon-enrichment, and phase in resonance with the pattern and micro- and nano-structural modifications. Through the application of modulated pulse sequences, in some embodiments, the laser-processed surface layer can be enriched in carbon and precisely varied from an oxygen/carbon ratio of 0.28 to an oxygen/carbon ratio of 0.20. This capability can enable laser-scripted conversion of PEEK from a fully insulating material to a highly efficient conductor, thereby defining interfacial regulation of electrical conductivity. For example, FIG. 6D is a graphical representation of measured resistance (kilo-ohm (k-ohm)) vs. laser fluence (mJ)/(cm)² using laser pulse script sequences under ambient and various gas purging conditions, including oxygen and argon. As illustrated in FIG. 6D, laser pulse-scripted processing can be used to variably convert PEEK from a fully insulating material to a highly efficient conductor, which can enable interfacial regulation of electric conductivity. As shown in FIG. 6D, the resistivity can be altered by a factor of more than one million, and the laser-scripted processing of the electrical inductions can take the form of electric field gradients, thereby enabling the creation of patterned in situ electric field dynamics that mitigate the need for activation via external stimulation.

Exemplary embodiments of the systems, assemblies, and methods are described above in detail. The systems, assemblies, and methods are not limited to the specific embodiments described herein, but rather, components of the systems, assemblies and/or steps of the method may be utilized independently and separately from other components and/or steps described herein. For example, the assembly may also be used in combination with other systems and methods, and is not limited to practice with only a system as described herein. Rather, the exemplary embodiment can be implemented and utilized in connection with many other systems.

Although specific features of various embodiments of the invention may be shown in some drawings and not in others, this is for convenience only. In accordance with the principles of the invention, any feature of a drawing may be referenced and/or claimed in combination with any feature of any other drawing.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

What is claimed is:

1. A material modification assembly comprising:
an energy source configured to generate a plurality of light beams for a modification to a material substrate: and
a computing device coupled to said energy source, wherein said computing device configured to:
generate at least one pattern script for the modification to the material substrate, wherein the at least one pattern script is based on at least one parameter of the modification;
generate at least one process script that includes a type of a plurality of pulse scripts to be used in conjunction with the plurality of light beams generated by said energy source for the modification to the material substrate, wherein the plurality of pulse, scripts are based on at least one parameter of the interaction between said energy source and the material substrate;
combine the at least one pattern script with the at least one process script such that the at least one pattern script and the at least one process script are interleaved, thereby generating a master control code, wherein the at least one pattern script and the at least one process script are linked, in an a line-by-line arrangement such that, when the material substrate undergoes the modification, a plurality of patterns are defined on at least a surface of the material substrate and the plurality of patterns are one of discretely spaced or separated;
generate a plurality of command signals that are based on the master control code; and
transmit the plurality of command signals to one or more additional component devices of said material modification assembly that are coupled to said computing device to enable the one or more component devices to facilitate modifying the plurality of light least one pattern of the plurality of patterns has dimensions and includes two or more discrete material alterations or changes spatially overlapped within the at least one pattern.

2. A material modification assembly in accordance with claim 1, further comprising a motion control system coupled to said computing device, wherein said motion control system is configured to receive at least one of the plurality of command signals and to generate at least one output that provides instructions for the type of the plurality of pulse scripts to use for the modification to the material substrate based on the at least one command signal.

3. A material modification assembly in accordance with claim 2, wherein said motion control system is further configured to translate a sample portion of the material substrate into a three-dimensional coordinate system.

4. A material modification assembly in accordance with claim 2, further comprising a waveform generator coupled to said motion control system, wherein said waveform generator is configured to generate the plurality of pulse scripts based on the at least one output such that the plurality of pulse scripts are enabled to be used with the plurality of light beams generated by said energy source for the modification to the material substrate.

5. A material modification assembly in accordance with claim 4, further comprising an amplifier coupled to said waveform generator, wherein said amplifier is configured to amplify the plurality of pulse scripts.

6. A material modification assembly in accordance with claim 5, further comprising one or more modulating devices coupled to said amplifier, wherein said one or more modulating devices are configured to combine the plurality of amplified pulse scripts with the plurality of light beams generated by said energy source.

7. A material modification assembly in accordance with claim 1, further comprising a detection device coupled to said computing device and positioned proximate to the material substrate, wherein said detection device is configured to:
   detect at least one parameter of the modification to the material substrate in real-time; and
   transmit a signal to said computing device representative of the detected at least one parameter of the modification to enable said computing device to generate an updated at least one pattern script and an updated at least one process script that are based on the detected at least one parameter.

8. A method for use in a modification of a material substrate, said method comprising:
   coupling an energy source to a computing device;
   generating at least one pattern script for a modification to a material substrate, via the computing device, wherein the at least one pattern script is based on at least one parameter of the modification;
   generating at least one process script that includes a type of a plurality of pulse scripts to be used in conjunction with a plurality of light beams generated by the energy source for the modification to the material substrate, via the computing device, wherein the plurality of pulse scripts are based on at least one parameter of the interaction between the energy source and the material substrate;
   combining the at least one pattern script with the at least one process script, via the computing device, thereby generating a master control code, such that the at least one pattern script and the at least one process script are interleaved, wherein the at least one pattern script and the at least one process script are linked, in a line-by-line arrangement such that, when the material substrate undergoes the modification, a plurality of patterns are defined on at least a surface of the material substrate and the plurality of patterns are one of discretely spaced or separated;
   generating a plurality of command signals that are based on the master control code, via the computing device; and
   transmitting the plurality of command signals to one or more additional component devices that are coupled to the computing device to enable the one or more component devices to facilitate modifying the plurality of light beams being generated by the energy source for the modification to the material substrate such that at least one pattern of the plurality of patterns has dimensions and includes two or more discrete material alterations or changes spatially overlapped within the at least one pattern.

9. A method in accordance with claim 8, wherein transmitting the plurality of command signals comprises transmitting at least one of the plurality of command signals to a motion control system that is coupled to the computing device.

10. A method in accordance with claim 9, further comprising translating a sample portion of the material substrate into a three-dimensional coordinate system, via the motion control system.

11. A method in accordance with claim 9, further comprising generating at least one output that provides instructions for the type of the plurality of pulse scripts to use for the modification to the material substrate based on the at least one command signal, via the motion control system.

12. A method in accordance with claim 11, further comprising:
   transmitting the at least one output to a waveform generator that is coupled to the motion control system; and
   generating the plurality of pulse scripts based on the output such that the plurality of pulse scripts are enabled to be used with the plurality of light beams generated by the energy source for the modification to the material substrate.

13. A method in accordance with claim 12, further comprising:
   transmitting the plurality of pulse scripts to an amplifier that is coupled to a waveform generator; and
   amplifying the plurality of pulse scripts via the amplifier.

14. A method in accordance with claim 13, further comprising:
   transmitting the amplified pulse scripts to one or more modulating devices coupled to the amplifier; and
   combining the plurality of amplified pulse scripts with the plurality of light beams generated by the energy source.

15. A method in accordance with claim 8, further comprising:
   detecting at least one parameter of the modification to the material substrate in real-time via a detection device that is coupled to the computing device and positioned proximate to the material substrate;
   transmitting a signal representative of the detected at least one parameter of the modification to the computing device; and
   generating an updated at least one pattern script and an updated at least one process script that are based on the detected at least one parameter, via the computing device.

16. A system comprising:
   a material substrate;
   a material modification assembly positioned proximate to said material substrate, said material modification assembly comprising:
   an energy source positioned proximate to said material substrate, wherein said energy source is configured to generate a plurality of light beams for a modification to said material substrate; and
   a computing device coupled to said energy source, wherein said computing device configured to:
   generate at least one pattern script, for the modification to said material substrate, wherein the at least one pattern script is based on at least one parameter of the modification;
   generate at least one process script that includes a type of a plurality of pulse scripts to he used in conjunction with the plurality of light beams generated by said energy source for the modification to said material substrate, wherein the plurality of pulse scripts are based on at least one parameter of the interaction between said energy source and said material substrate:
   combine the at least one pattern script with the at least one process script such that the at least one pattern script and the at least one process script are interleaved, thereby generating a master control code, wherein the at least one pattern script and the at least one process script are linked, in a line-by-line arrangement such that, when the material substrate undergoes the modification, a plurality of patterns are defined on at least a surface of the material substrate and the plurality of patterns are one of discretely spaced or separated;

generate a plurality of command signals that are based on the master control code; and transmit the plurality of command signals to one or more additional component devices of said material modification assembly that are coupled to said computing device to enable the one or more component devices to facilitate modifying the plurality of light beams being generated by said energy source for the modification to said material substrate such that at least one pattern of the plurality of patterns has dimensions and includes two or more discrete material alterations or changes spatially overlapped within the at least one pattern.

17. A system in accordance with claim 16, wherein said material modification assembly further comprises a motion control system coupled to said computing device, wherein said motion control system is configured to receive at least one of the plurality of command signals and to generate at least one output that provides instructions for the type of the plurality of pulse scripts to use for the modification to said material substrate based on the at least one command signal.

18. A system in accordance with claim 17, wherein said motion control system is further configured to translate a sample portion of said material substrate into a three-dimensional coordinate system.

19. A system in accordance with claim 17, wherein said material modification assembly further comprises a waveform generator coupled to said motion control system, wherein said waveform generator is configured to generate the plurality of pulse scripts based on the at least one output such that the plurality of pulse scripts are enabled to be used with the plurality of light beams generated by said energy source for the modification to said material substrate.

20. A system in accordance with claim 19, wherein said material modification assembly further comprises an amplifier coupled to said waveform generator, wherein said amplifier is configured to amplify the plurality of pulse scripts.

21. A system in accordance with claim 20, wherein said material modification assembly further comprises one or more modulating devices coupled to said amplifier, wherein said one or more modulating devices are configured to combine the plurality of amplified pulse scripts with the plurality of light beams generated by said energy source.

22. A system in accordance with claim 16, wherein said material modification assembly further comprises a detection device coupled to said computing device and positioned proximate to said material substrate, wherein said detection device is configured to:

detect at least one parameter of the modification to said material substrate in real-time; and transmit a signal to said computing device representative of the detected at least one parameter of the modification to enable said computing device to generate an updated at least one pattern script and an updated at least one process script that are based on the detected at least one parameter.

* * * * *